(12) United States Patent
Li et al.

(10) Patent No.: US 9,018,950 B2
(45) Date of Patent: Apr. 28, 2015

(54) SPIN ECHO SPI METHODS FOR QUANTITATIVE ANALYSIS OF FLUIDS IN POROUS MEDIA

(76) Inventors: Linqing Li, Oxford (GB); Bruce Balcom, Frederiction (CA); Derrick Green, Fredericton (CA); Oleg Petrov, Fredericton (CA)

( * ) Notice: Subject to any disclaimer, the term of this patent is extended or adjusted under 35 U.S.C. 154(b) by 693 days.

(21) Appl. No.: 13/003,529

(22) PCT Filed: Jul. 8, 2009

(86) PCT No.: PCT/CA2009/000943
§ 371 (c)(1), (2), (4) Date: Apr. 4, 2011

(87) PCT Pub. No.: WO2010/003236
PCT Pub. Date: Jan. 14, 2010

(65) Prior Publication Data
US 2011/0204892 A1 Aug. 25, 2011

Related U.S. Application Data

(60) Provisional application No. 61/079,106, filed on Jul. 8, 2008, provisional application No. 61/080,831, filed on Jul. 15, 2008.

(51) Int. Cl.
*G01R 33/50* (2006.01)
*G01V 3/32* (2006.01)
(Continued)

(52) U.S. Cl.
CPC ............... *G01V 3/32* (2013.01); *G01N 24/081* (2013.01); *G01N 24/085* (2013.01); *G01R 33/50* (2013.01); *G01R 33/5617* (2013.01)

(58) Field of Classification Search
USPC ........................... 324/300–322; 600/407–445
See application file for complete search history.

(56) References Cited

U.S. PATENT DOCUMENTS 5,289,124 A * 2/1994 Jerosch-Herold et al. ..... 324/303
5,387,865 A * 2/1995 Jerosch-Herold et al. ..... 324/303
(Continued)

FOREIGN PATENT DOCUMENTS

CA 2531072 A1 1/2005
CA 2634104 A1 12/2008

OTHER PUBLICATIONS

Linqing, L. et al., "Spin echo SPI methods for quantitative analysis of fluids in porous media" Journal of Magnetic Resonance, vol. 198, Issue 2, Jun. 2009, pp. 252-260, Available on-line Mar. 9, 2009.
(Continued)

*Primary Examiner* — Dixomara Vargas
(74) *Attorney, Agent, or Firm* — Eugene F. Derényi; Fogler, Rubinoff LLP

(57) ABSTRACT

A method of measuring a parameter in a sample by imaging at least a portion of the sample using a spin-echo single-point imaging (SE-SPI) pulse sequence. This method involves applying a pure phase encoding to the SE-SPI pulse sequence, acquiring a multiplicity of echoes, and determining the spatially resolved T2 distribution. In another embodiment, individual echoes are separately phase encoded in a multi-echo acquisition and the SE-SPI pulse sequence is a hybrid SE-SPI sequence. In another embodiment, an external force can be used to build up a distribution of saturations in the sample, and a T2 distribution can be measured for the sample, which is then used to determine a parameter of the sample. A spatially resolved T2 distribution can also be measured and a resulting spatially resolved T2 distribution used to determine the T2 distribution as a function of capillary pressure.

18 Claims, 12 Drawing Sheets

(51) Int. Cl.
G01N 24/08 (2006.01)
G01R 33/561 (2006.01)

(56) References Cited

U.S. PATENT DOCUMENTS

| | | | |
|---|---|---|---|
| 5,486,762 A * | 1/1996 | Freedman et al. | 324/303 |
| 5,561,370 A * | 10/1996 | Fuderer | 324/309 |
| 6,263,228 B1 | 7/2001 | Zhang et al. | |
| 6,956,370 B2 | 10/2005 | Heidler | |
| 7,753,119 B2 * | 7/2010 | Chen et al. | 166/250.1 |
| 2013/0057277 A1 * | 3/2013 | Zielinski et al. | 324/303 |
| 2013/0221963 A1 * | 8/2013 | Serra | 324/309 |

OTHER PUBLICATIONS

ISA/CA. Written Opinion of the International Searching Authority Sep. 11, 2009.
Extended European Search Report Dated Feb. 24, 2013 for EP 09793752.8.
S. Chen, et al., "NMR Imaging of Multiphase Flow in Porous Media", Society of Petroleum Engineers, Oct. 4-7, 1992.
F. Marica, et al., "Spatially Resolved Measurement of Rock Core Porosity", J. Magn. Reson. 178(1): 136-141, Jan. 2006.
B. J. Balcom, et al., "Single-Point Ramped Imaging with T1 Enhancement (SPRITE)", J. Magn. Reson. A 123(1): 131-134, Nov. 1996.
Z. Zhang, et al., "Spatial and Temporal Mapping of Water Content Across Nafion Membranes Under Wetting and Drying Conditions", J. Magn. Reson. 194(2): 245-253, Oct. 2008.
S. Gravina and D. G. Cory, "Sensitivity and Resolution of Constant-Time Imaging", J. Magn. Reson. B 104(1): 53-61, May 1994.
Y. Cheng, et al., "Direct Detection of Hydrocarbon Displacement in a Model Porous Soil with Magnetic Resonance Imaging", Anal. Chem. 77(6): 1824-1830, Mar. 2005.
Y. Cheng, "Carbon-13 Magnetic Resonance Imaging of Physico-Chemical Processes", (Ph.D Thesis), University of New Brunswick (2006).
A. V. Ouriadov, et al., "Thin Film MRI—High Resolution Depth Imaging with a Local Surface Coil and Spin Echo SPI", J. Magn. Reson. 169(1): 174-186, Jul. 2004.
S. D. Beyea, et al., "Imaging of Heterogeneous Materials with a Turbo Spin Echo Single-Point Imaging Technique", J. Magn. Reson. 144(2): 255-265, Jun. 2000.
R. L. Kleinberg, et al., "Mechanism of NMR Relaxation of Fluids in Rock", J. Magn. Reson. A108(2): 206-214, Jun. 1994.
Y. Q. Song, et al., "Determining Multiple Length Scales in Rocks", Nature 406(6792): 178-181, Jul. 2000.
R. L. Kleinberg, "Utility of NMR T2 Distribution, Connection with Capillary Pressure, Clay Effect, and Determination of the Surface Relaxivity Parameter p2", Magn. Reson. Imaging 14(7-8): 761-767 (1996).
D. Chang, et al., "Effective Porosity, Producible Fluid and Permeability in Carbonates from NMR Logging", SPWLA 35 Annual Logging Symposium (1994).
G. R. Coates, et al., "A New Characterization of Bulk-Volume Irreducible Using Magnetic Resonance", SPWLA 38 Annual Logging Symposium (1997).
C. S. Poon and R. M. Henkelman, "Practical T2 Quantitation for Clinical Applications", J. Magn. Reson. Imaging 2 (5): 541-553, Sep. 1992.
A. P. Crawley et al., "Elimination of Transverse Coherences in FLASH MRI", Magn. Reson. Med. 8(3): 248-260, Nov. 1988.
A. A. Maudsley, "Modified Carr-Purcell-Meiboom-Gill Sequence for NMR Imaging Fourier Imaging Applications", J. Magn. Reson. 69(3): 488-491, Oct. 1986.
L. L. Latour et al., "Pore-Size Distributions and Tortuosity in Heterogeneous Porous Media", J. Magn. Reson. A 112 (1): 83-91, Jan. 1995.
R. L. Kleinberg and M. A. Horsfield, "Transverse Relaxation Processes in Porous Sedimentary Rock", J. Magn. Reson. 88(1): 9-19, Jun. 1990.
P. Wong, (1999). "Methods in the Physics of Porous Media", (vol. 35, pp. 337-385), N.P.: Academic Press, Cover Page, Table of Contents p. v and Chapter 9.
D. J. Goodyear et al., "Single Point Measurements of Magnetic Field Gradient Waveform", J. Magn. Reson. 163(1): 1-7, Jul. 2003.
K. Deka et al., "Quantitative Density Profiling with Pure Phase Encoding and a Dedicated 1D Gradient", J. Magn. Reson. 178(1): 25-32, Jan. 2006.
M. C. Jeruchim et al., (1992), "Simulation of Communication Systems", N.p.: Plenum Press, Cover page, Table of Contents and p. 1.
Q. Chen and B. J. Balcom, "Measurement of Rock Core Capillary Pressure Curves Using a Single-Speed Centrifuge and One Dimensional Magnetic Resonance Imaging", J. Chem. Phys. 122(21): 214720, Jun. 2005.
L. W. Lake, (2007), "Petroleum Engineering Handbook", (E. D. Holstein vol. 5, "Reservoir Engineering and Petrophysics" pp. 289-356), N.p.: Society of Petroleum Engineers.
M. H. Levitt, "Composite Pulses", Prog. in Nucl. Magn. Reson. Spec. 18(2): 61-122 (1986).
C. W. Windt et al., "Correlated Displacement-T2 MRI by Means of a Pulsed Field Gradient-Multi Spin Echo Method", J. Magn. Reson. 185(2): 230-239, Apr. 2007.
X. Wan et al., "Reduction of Phase Error Ghosting Artifacts in Thin Slice Fast Spin-Echo Imaging", Magn. Reson. Med. 34(4): 632-638, Oct. 1995.
T. Gullion, "The Effect of Amplitude Imbalance on Compensated Carr-Purcell Sequences", J. Magn. Reson. A101 (3): 320-323, Feb. 1993.
H. T. Edzes et al., "Quantitative T2 Imaging of Plant Tissues by Means of Multi-Echo MRI Microscopy", Magn. Reson. Imaging 16(2): 185-196 (1998).
O. Petrov, "A Comparison of Two Pulse Sequences for 1-D T2 Mapping with a Purely Phase Encoding: One is an 'Encode Once' Sequence with a XY-16 Phase Cycle and the Other is an 'Encode in Every Pulse Interval' Sequence with a CPMG Phase Cycle", Report, UNB MRI Centre (2009).
K. Deka et al., "Spatial Mapping of Solid and Liquid Lipid in Confectionery Products Using a 1D Centric SPRITE MRI Technique", Food Research Inter. 39(3): 365-371, Apr. 2006.
Prado P J et al."Spatially resolved relaxometry and pore size distribution by singly-point MRI methods; porous media calorimetry"; Journal of Physics D (Applied Physics) IOP Publishing US, vol. 31, No. 16. Aug. 21, 1998, pp. 2040-2050.

* cited by examiner (a)

(b)

(c)

(d)

(a)

(b)

(c)

SPIN ECHO SPI METHODS FOR QUANTITATIVE ANALYSIS OF FLUIDS IN POROUS MEDIA

FIELD OF THE INVENTION

The present invention relates to NMR measurement methods in porous media.

BACKGROUND OF THE INVENTION

Quantitative MRI methods applied to porous media have the potential to determine a wide variety of valuable petrophysical properties [1]. Most MRI methods feature inherent relaxation time contrast and in many instances this is considered a positive feature. However, core analysis of fluid properties of porous media frequently requires true fluid content images [2].

The SPRITE class of MRI methods have proven to be robust and general in their ability to generate fluid content images [3] in porous media. However, the short encoding times required, with correspondingly high magnetic field gradient strengths and filter widths, and low flip angle RF pulses, yield sub-optimal S/N images, especially at low static field strength.

Spin echo single point imaging ("SE-SPI") has inherently good S/N due to a relatively narrow signal bandwidth [4]. Lacking magnetic field gradients at the k-space origin, the imaging experiment will not suffer significant diffusive attenuation [5]. In previous work, SE-SPI has proven very successful in cases where the inherent S/N is poor, such as natural abundance $^{13}$C imaging [6], $^{13}$C gas phase imaging [7] and high resolution thin film imaging [8]. In addition, as a pure phase encoding technique, SE-SPI is largely immune to image distortion due to susceptibility variation and paramagnetic impurities in porous media.

A simple density image of fluid distribution in porous media, with no relaxation time contrast, is remarkably difficult to achieve with conventional methods. Short transverse relaxation lifetimes ($T_2$) yield signal loss while multi exponential $T_1$ and $T_2$ yield variable signal attenuation in a simple spin echo image.

SUMMARY OF THE INVENTION

In the present invention, SE-SPI and turbo SE-SPI methods [9] are modified to create a new imaging method, termed hybrid SE-SPI. The k-space origin data point is acquired with a near zero evolution time from the FID following the 90° excitation pulse. At k=0, no gradient is applied and the k=0 data point has a pure density weighting. Subsequent k-space data points do suffer from $T_2$ attenuation but the echo time may be reduced to 1 ms or less with rapid gradient switching. $T_2$ attenuation of the pure phase encoded echoes introduces a convolution to the subsequent density weighted image. In hybrid SE-SPI, $T_2$ is no longer an uncontrolled contrast parameter, it is a blurring parameter.

While fluid content is important for quantitative analysis of porous media, the most common MR measurement in porous media is a relaxation time distribution measurement [10]. Such measurements can determine the pore size distribution over several orders of magnitude in [11]. Properties derived from the NMR-determined pore size distribution include hydraulic permeability, capillary bound water saturation, residual oil saturation and gas volume [12]. Permeability prediction from the $T_2$ distribution has been adopted as a successful reservoir well logging technology [13].

One aspect of this invention is a method of measuring a parameter, such as fluid content, in a sample by imaging at least a portion of the sample using a spin-echo single-point imaging (SE-SPI) pulse sequence comprising the steps of applying a pure phase encoding to the SE-SPI pulse sequence, acquiring a multiplicity of echoes, and determining the spatially resolved $T_2$ distribution. A phase encoding and phase unwinding gradient can be applied to each spin-echo using a Carr-Purcell-Meiboom-Gill (CPMG) multi-echo sequence between refocusing pulses in the CPMG sequence. Fixed RF pulse phases can be used in the CPMG sequence and the fluid content can be spatially resolved for the sample.

In another embodiment of the invention, the step of applying the pure phase encoding comprises applying a phase encoding gradient to the SE-SPI pulse sequence using an XY-16 sequence and composite RF pulses. The phase encoding gradient can be applied once during the SE-SPI pulse sequence or after the first inter-pulse delay of the SE-SPI pulse sequence.

In one embodiment, the sample is porous media and is at least partially saturated with a fluid.

In yet another embodiment, an external force is used to build up a distribution of saturations in one dimension in the sample, a $T_2$ distribution for the sample is measured, and the $T_2$ distribution is used to determine a parameter of the sample.

In a further embodiment, a spatially resolved $T_2$ distribution is measured for the sample, and a resulting spatially resolved $T_2$ distribution is used to determine the $T_2$ distribution as a function of capillary pressure. An image of a local saturation of the sample can also be generated by integration of the $T_2$ distribution curve or by fitting the spatially resolved decay curve to three exponentials and extrapolating to zero. The local log mean $T_2$ distribution can be correlated with local saturation to characterize the sample.

In yet a further embodiment, the step of applying the pure phase encoding comprises separately phase encoding individual echoes in a multi-echo acquisition and wherein the SE-SPI pulse sequence is a hybrid SE-SPI sequence.

In another aspect, the present invention relates to a method of extracting information about a system of nuclear spins using a measurement that is a series of RF excitations, the first excitation being such that the signal acquired after the first excitation is largely proportional to the total number of nuclear spins, and wherein pulse magnetic field gradients are applied during subsequent excitations such that positional information is encoded into the phase of the acquired data.

In another aspect, the present invention relates to a method of extracting information about a system of nuclear spins using a measurement that is a series of RF excitations wherein the excitations form signal echoes that decay away with the time constant of $T_2$, and repeating the series of excitation with different amplitudes of magnetic field gradients applied during the echoes such that sample spatial information is encoded in to the phase of the detected signals. In one embodiment, the foregoing method can be used with a conventional centrifuge to build up a distribution of saturation in a rock sample and measuring it to obtain a $T_2$ distribution at various saturations to obtain a permeability model for the rock sample or an irreducible saturation for the rock sample or another parameter of the sample.

In a further aspect, the present invention relates to a method of extracting information about a porous media comprising the steps of (a) using an external force to build up a distribution of saturations in a porous media in one dimension, (b) extracting information about a system of nuclear spins using a measurement that is a series of RE excitations wherein the excitations form signal echoes that decay away with the time constant of $T_2$, repeating the series of excitation with different amplitudes of magnetic field gradients applied during the echoes such that sample spatial information is encoded in to the phase of the detected signals, whereby a series of spatial $T_2$ distributions at different spatial locations that correspond to the different saturation levels introduced by step (a) is acquired, and (d) using the $T_2$ distribution to extract one or more parameters about the porous media.

According to one aspect, the present invention relates to a hybrid spin echo single point imaging ("hybrid SE-SPI") method for acquisition of fluid content images. Because a short time evolution FID point is used as the k-space origin data point, images acquired are substantially contrast free. In one embodiment, the methods of the present invention may be used for quantitative image acquisition for fluid content in porous media, especially for fluid quantification in petroleum core plug analysis where the mean $T_2$ of the core plug is longer than 5 ms.

According to another aspect, the present invention relates to an improved method which permits fast determination of spatially resolved $T_2$ distributions in porous media with echo times of 1 ms or less. The methods of the present invention permit generation of several thousand $T_2$ weighted images in several minutes. Given the short echo time and low field, the transverse time distribution is a reflection of the fluid occupied pore size distribution.

In one embodiment, a practical application of the methods according to the present invention is imaging a centrifuged core plug.

In another embodiment of the present invention, the logarithm mean $T_2$ calculated from the $T_2$ distribution of individual pixels on the core plug varies linearly with the pixel water saturation. An empirical equation for prediction of the water irreducible saturation (SWIRR) has been derived from permeability models.

In another aspect, the present invention relates to a new implementation of SE-SPI, termed $T_2$ mapping SE-SPI, which permits fast 1D $T_2$ weighted images for the determination of spatially resolved $T_2$ distributions in porous media. The method features echo times which may be reduced to 1 ms or less. In a further aspect, $T_2$ weighted profiles may then be fit to extract a $T_2$ distribution, pixel by pixel, employing a variety of standard inverse Laplace transform methods. Fluid content 1D images are produced as an essential by-product of determining the spatially resolved $T_2$ distribution. These 1D images do not suffer from a $T_2$ related blurring.

In another aspect of the present invention, the present invention relates to an improved SE-SPI method for acquiring the k-space origin data point with a near zero evolution time from the free induction decay (HD) following a 90° excitation pulse. Subsequent k-space data points are acquired by separately phase encoding individual echoes in a multi-echo acquisition. $T_2$ attenuation of the echo train yields an imaging convolution which causes blurring. The $T_2$ blur effect is moderate for porous media with $T_2$ lifetime distribution larger than 5 ms. As a robust, high S/N, and fast 1D imaging method, this method is complimentary to SPRITE techniques for the quantitative analysis of fluid content in porous media.

In another aspect, the present invention relates to an improved SE-SPI measurement which permits fast determination of spatially resolved $T_2$ distributions in porous media. The echo time (TE) of each of these $T_2$ weighted images is reduced to 1 ms or less. These profiles can be used to extract a $T_2$ distribution from each pixel using a variety of standard inverse Laplace transform programs.

The value of a spatially resolved $T_2$ measurement in reservoir core analysis is demonstrated through measurement of a centrifuged reservoir core plug. A linear relationship between the local water saturation and the logarithm mean $T_2$ is observed. The linear relationship is predicted based on a simple derivation. The linear relationship produces a fast calibration procedure for the Coates equation describing the irreducible water saturation (SWIRR) of importance to NMR well logging. It would be desirable to have a faster, simpler, and more reliable and accurate method to the SWIRR calibration procedure [14].

In a further aspect, the present invention relates to a method for imaging the local saturation and $T_2$ distribution as a function of saturation, upon centrifuging petroleum reservoir core samples. The logarithms mean $T_2$ is observed to shift linearly with saturation. This measurement may provide a valuable calibration procedure for determination of the irreducible water saturation which has widely been implemented in NMR well logging measurements.

DETAILED DESCRIPTION OF THE PREFERRED EMBODIMENTS

A. Hybrid SE-SPI

Figure 1:
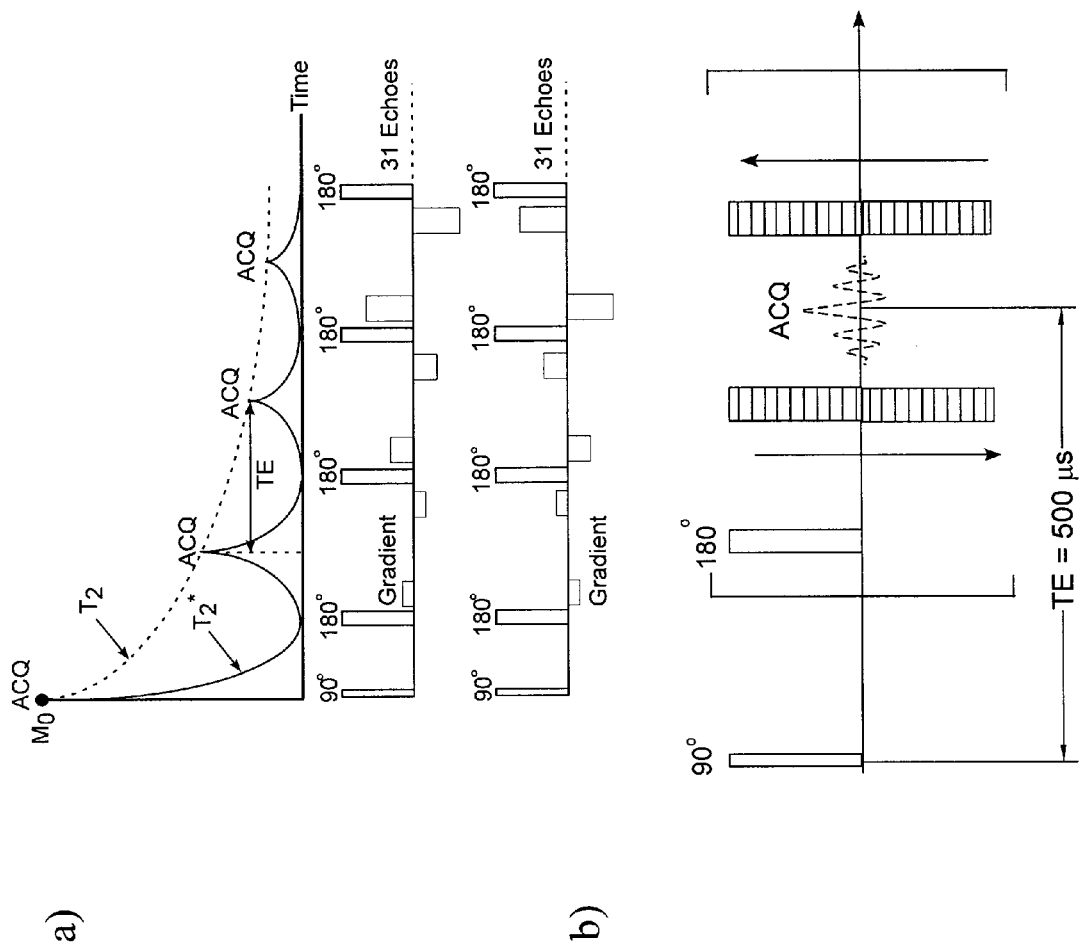
FIG. 1a is a graph showing a 1D hybrid SE-SPI pulse sequence for fluid content imaging of fluids in porous media.
FIG. 1b is a diagram showing a 1D spatially resolved $T_2$ mapping measurement.

FIG. 1(a) is a graph showing a 1D hybrid SE-SPI pulse sequence for fluid content imaging of fluids in porous media. The k=0 point is taken at a very short evolution time on the FID. Subsequent k-space points are taken from individual pure phase encoded echoes with the phase unwrapped following each echo.

The hybrid SE-SPI pulse sequence in FIG. 1a is capable of obtaining near zero relaxation time weighted images of fluids in porous media. The 1D k-space points are acquired in two separate acquisitions with a 5 times $T_1$ delay between them to ensure full longitudinal magnetization recovery, and no $T_1$ weighting. The phase encoding for each echo is removed by an identical gradient pulse of altered sign immediately after the echo. Each k-space acquisition starts from k=0 then proceeds to higher order k-space points in the positive or negative direction. The two k-space segments may then be combined into a 1D k-space data set for Fourier transformation and image reconstruction. The k=0 data point is the averaged value from the two acquisitions. The overall image intensity is determined by the intensity of the k=0 data point. Frequency encoded or phase encoded spin echo images have a local image intensity defined by Eq (1).

$$S(y) = \rho_0(y)\exp\left(-\frac{nTE}{T_2(y)}\right) \quad (1)$$

In Eq (1), n is the echo number corresponding to the center of k-space, while TE is the echo time. The image intensity S(y) is defined by the product of the spin density, $\rho_0(y)$, and $T_2$ weighting in the exponential term. From FIG. 1a, the $T_2$ weighting will be simply removed due to taking the first point of the free induction decay (FID) as k=0. In this case, n is equal to zero such that the intensity S(y) in Eq (1) will be simply equal to the spin density $\rho_0(y)$.

Blurring in Hybrid SE-SPI

Amplitude modulation of the true k-space data, defined by the modulation transfer function (MTF), leads to blurring and other image artifacts. The pulse sequence of FIG. 1a will lead to an exponential decay of the modulation transfer function, and a simple image blurring. The blurring may be quantified by the point spread function (PSF). Severe blurring may cause sufficient degradation that it will affect quantification of hybrid SE-SPI images. The overall MTF and PSF are determined by Eq (2) and (3) where the multiplications in Eq (2) become convolutions in Eq (3).

$$MTF = MTF_{k\text{-}space} \times MTF_{diffusion} \times MTF_{T_2} \quad (2)$$

$$PSF = PSF_{k\text{-}space} \otimes PSF_{diffusion} \otimes PSF_{T_2} \quad (3)$$

$MTF_{k\text{-}space}$ is the MTF due to k-space sampling, usually with 64 data points. $MTF_{T_2}$ is due to the signal amplitude decay with time constant $T_2$. Because acquisition of the $MTF_{T_2}$ function is symmetric, the corresponding PSF will be Lorentzian (for single exponential $T_2$). $MTF_{diffusion}$ is the MTF due to molecular diffusion through underlying magnetic field gradients which will be limited by decreasing the echo time (TE). Ideally, the limiting resolution will be simply determined by the size of the sampled k-space. The most significant blurring in hybrid SE-SPI image will be due to the $MTF_{T_2}$ and $PSF_{T_2}$ depending on the weighting of the short $T_2$ components in the $T_2$ distribution. Decreasing the experimental echo time will attenuate the decay and decrease the blurring.

NMR measurements are particularly important in oil and gas reservoirs to measure both porosity and pore sizes in the reservoir. The amplitude of the spin-echo-train decay can be fit very well by a sum of decaying exponentials, each with a different decay constant. Reservoir rocks generally contain a distribution of pore sizes and potentially more than one fluid. Therefore, the spin-echo train recorded with a CPMG sequence does not decay with a single T2 value but instead with a distribution of T2 values.

B. $T_2$ Mapping SE-SPI

To generate spatially resolved $T_2$ distributions, one must have the ability to generate hundreds or thousands of profiles with very short echo times. The key problems in multi-echo MRI are well known [15]. Deviation from exact 180° refocusing pulses results in image artifacts from stimulated echoes. The modulation and cumulative loss of image intensity in successive echoes, and contamination of the $T_2$ relaxation with a $T_1$ contribution, must all be considered [16]. With very short echo times, for example 500 μs, eddy current problems due to fast gradient switching will cause significant trouble for high quality images. Consequently, multi-echo imaging is usually restricted to the acquisition of a limited number of echoes with relatively long echo times, and the measured $T_2$ values may show considerable scatter [17].

Imaging artifacts in multi-echo imaging are often suppressed by the use of spoiling gradients around the 180° pulses [18]. Alternatively, specific RF excitation phase cycles such as MLEV-4, -8 or -16, or XY-4, -8 or -16 [19] can be applied to counteract the cumulative effects of phase errors. The use of spoiling gradients causes cumulative loss of magnetization from successive echoes and after a large number of echoes, the observed $T_2$ is reduced [20]. These methods are not employed in the methods according to the present invention.

A modified SE-SPI imaging pulse sequence, as shown in FIG. 1b is used for $T_2$ mapping. The echo time in each case was 500 μs. The phase encoding and phase unwinding gradients are applied around each echo with simple CPMG refocusing. By applying the phase encoding gradient for each echo, the stimulated echoes due to imperfect 180° pulses are removed and this helps ensure an accurate $T_2$ measurement [19].

$T_2$ Distribution in Porous Media at Low Field

Bulk CPMG measurements to determine the $T_2$ distribution in porous media are usually undertaken with echo times less than 1 ms. Pore size can be determined only when the pore space is saturated with the wetting phase fluid and the relaxation behavior is dominated by surface relaxation [21]. Decreasing the deleterious effects due to diffusion through internal, field gradients requires low field measurement with short echo spacing. For rocks, it has been reported that even at low fields, a 1 ms echo time in porous media may change the CPMG decay due to diffusion through internal field gradients [22]. If fluid saturation is reduced, $T_1$ and $T_2$ lifetimes are typically shifted to shorter times [23].

EXAMPLES

A. Hybrid SE-SPI
Core Plug Image by Hybrid SE-SPI

Figure 2:
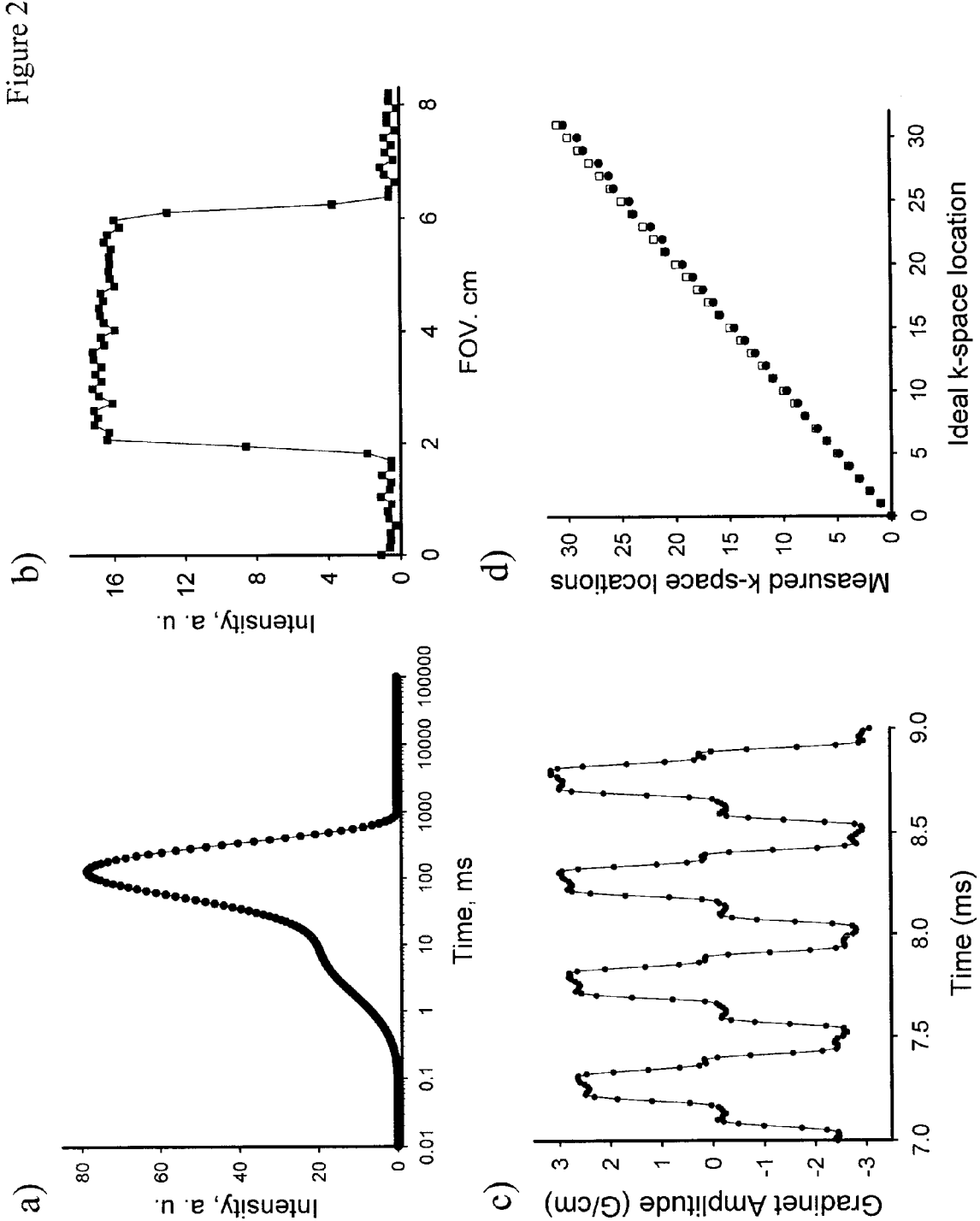
FIG. 2a is a graph showing bulk $T_2$ distribution of fully saturated sandstone sample #1, TE=500 µs, 1024 echoes.
FIG. 2b is a 1D image of sandstone #1 employing the hybrid SE-SPI technique with TE=500 µs.
FIG. 2c is a graph showing gradient waveform measurement from the $15^{th}$ to $18^{th}$ gradient lobes in a hybrid SE-SPI measurement.
FIG. 2d is a graph integrating positive gradient k-space points where • matches with the ideal case □.

Berea sandstone (sandstone #1) which has a typical sandstone $T_2$ distribution, shown in FIG. 2a, was imaged employing the pulse sequence of FIG. 1a. Acquired with 4 scans in 20 seconds at 0.35 T, the core plug image, FIG. 2b, is a high quality 1D fluid content image with an SNR of 32. As with all experimental and simulated images in the embodiments of this invention, the imaging axis is longitudinal to the sample.

The high quality profile, at short echo time results from the pure phase encoding nature of this experiment. In a phase encoding experiment, it is the increment in gradient area that is most important, not a high fidelity gradient waveform. The gradient waveform was measured employing the methodology of reference [24]. FIG. 2c shows that with a phase encoding time ($t_p$) as short as 150 μs, distortion in the gradient waveform is inevitable. The gradient waveform in FIG. 2c would induce artifacts in a frequency encoding imaging measurement which relies on a constant gradient while sampling k-space. The gradient waveform is non-ideal but k-space sampling is still regular.

Unlike frequency encoding methods, SE-SPI is robust to distortion of the gradient waveform because SE-SPI requires only that the gradient area increment regularly. An integration of the gradient waveform for each positive k-space step is displayed in FIG. 2d and compared to the ideal case. The gradient area increment is close to ideal, as is the gradient cancellation of each phase encode step.

Image Sensitivity

The double half k-space 1D SPRITE imaging method (DHK SPRITE) has proven to be a robust and general method to generate fluid content images (spin density images) in porous media [25]. However broad filter widths, and low flip angle RF pulses, yield sub-optimal S/N images. DHK 1D SPRITE and hybrid SE-SPI were employed to image core plug sandstone #1. As the basis of comparison, acquisition of images by the two methods signal was averaged to equivalent S/N. The sensitivity is defined as $$\eta = \frac{S/N}{\sqrt{t}} \quad (4)$$

where t is the total imaging time. A sensitivity comparison of the two profiles is shown in Table 1. The sensitivity η differs by a factor of 3. A DHK SPRITE image requires 10 times longer to acquire than a similar hybrid SE-SPI image of these samples at 15 MHz (0.35 T).

From Table 1, the filter chosen in SE-SPI is not optimized and it should be decreased further to improve the S/N ratio. Rather than optimizing the filter width and acquiring one point on the echo, a multiple point acquisition is likely an alternate method for S/N ratio enhancement.

It is estimated that at low magnetic field (0.35 T), given the same S/N, the hybrid SE-SPI technique might achieve high quality results, 20-30 times faster than SPRITE DHK imaging.

The SPRITE filter width in Table 1 is optimal based on the signal bandwidth at k-space extremities. The SE-SPI filter width in Table 1 is however not optimized. It could be narrowed in principle to the natural line width to increase the S/N as $1/\sqrt{FW}$. A potential problem associated with the narrow filter width is, however, an increased receiver deadtime. This deadtime could introduce a $T_2^*$ weighting into the images through the FID based k=0 data point. In the current experiment the filter width of 125,000 Hz had a deadtime of 26 μs. This causes minimal $T_2^*$ attenuation of the k=0 data point and is much less than the τ time (250 μs). In general the filter width is more of a $T_2^*$ concern than a limitation on the echo time. It should be possible to design a digital filter for this application which will simultaneously have a narrow bandwidth and short deadtime.

The choice of a SE-SPI filter that is too broad means the sensitivity comparison is even more in favor of SE-SPI than suggested by Table 1. A broad filter width however permits a very simple multiple point echo acquisition for S/N enhancement. A multiple point acquisition on each echo, averaging the resulting data points, is a better strategy for S/N enhancement. To ensure that the noise between data points is uncorrelated, the dwell time between points must be longer than the inverse of twice the filter width [26]. As an example of the potential benefits, the hybrid SE-SPI imaging experiment for sandstone #1 has a filter width of 125,000 Hz, and therefore a 4 μs dwell time. Based on the gradient waveform measurement of FIG. 2c, the stable gradient period is approximately 50 μs. Therefore at least 10 time domain points on the echo could potentially be acquired for S/N enhancement. This strategy is not implemented in the current work, but will be essential when translating these ideas to low field, 2 MHz, magnets which are industry standard for petroleum reservoir core analysis.

Hybrid SE-SPI $T_2$ Image Blurring $T_2$ attenuation of the pure phase encoded echoes, illustrated in FIG. 1a, introduces a convolution to the subsequent fluid content weighted 1D image. To simulate the extent of the $T_2$-blurring, a box car function with 5% noise, representing a 1D idealized image, has been calculated in FIG. 3a, 3b. The two boxcar images were convolved with $T_2$ decays of time constant 2 ms and 5 ms respectively.

The image comparison reveals that the simulated boxcar phantom, convolved with a 2 ms $T_2$ decay, has an image blurring unacceptable for image quantification. Note the spatial data points on the profile edge are significantly dislocated. The simulated images suggest that hybrid SE-SPI may be employed for porous media with significant $T_2$ components longer than 5 ms. Typical relaxation times for capillary bound water in petroleum samples are between 3 ms and 30 ms depending on the rock type [23]. The $T_2$ relaxation time distribution of FIG. 2a is very common for porous media; therefore, hybrid SE-SPI will likely be a general tool, although not universal, for fluid content imaging in porous media. Short $T_2$ components of sandstone sample #1, FIG. 2a, are blurred in the experimental image of FIG. 2b, however, the short relaxation time components are minor and the experimental image is not visibly affected.

Figure 3:
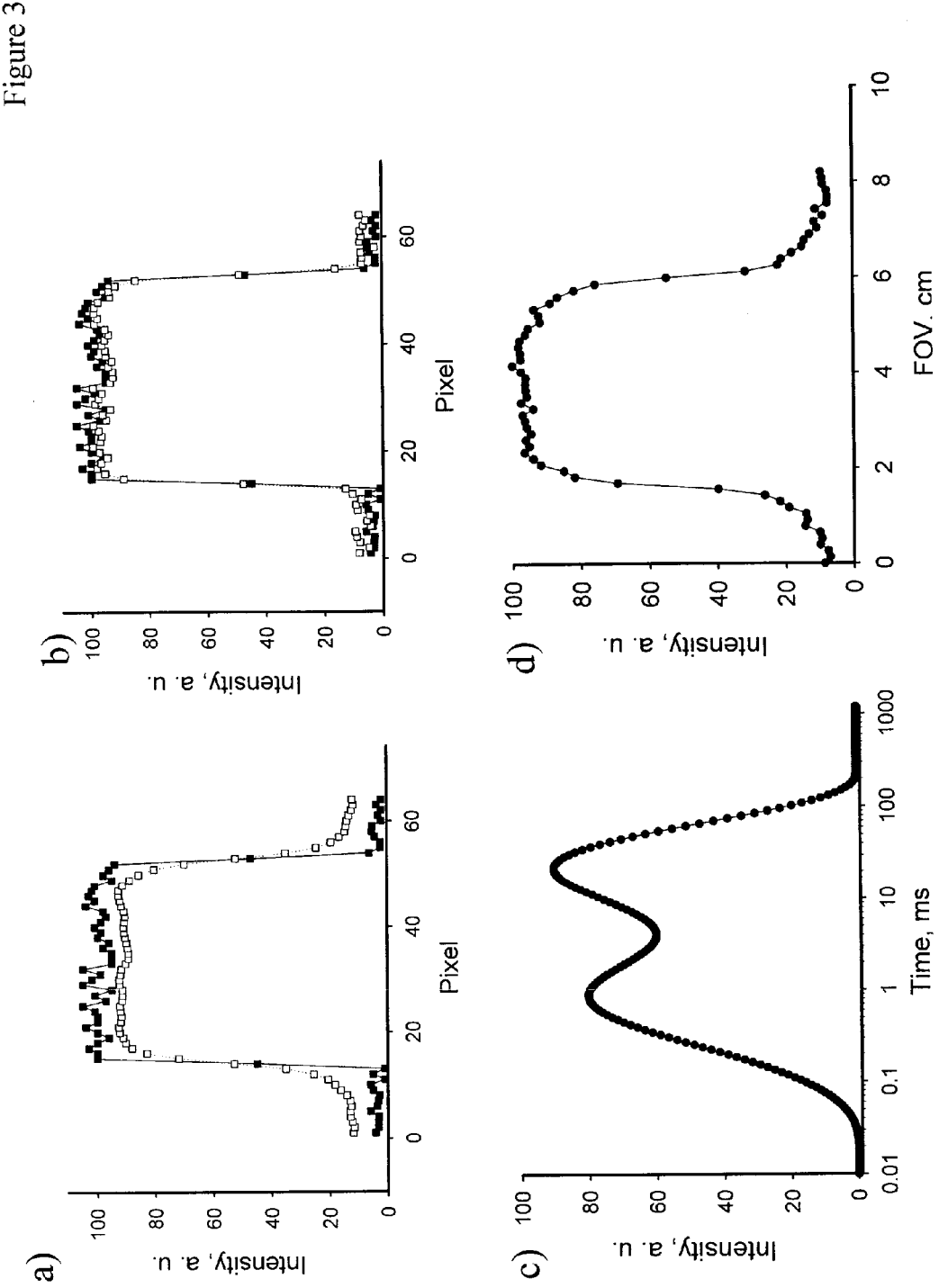
FIG. 3a is a graph showing simulated 1D images of a simple box car phantom with 5% noise ■ where images □ are the box car phantoms convolved with single exponential $T_2$ decay, 2 ms $T_2$ for measurement with TE=500 µs.
FIG. 3b is a graph showing simulated 1D images of a simple box car phantom with 5% noise ■ where images □ are the box car phantoms convolved with single exponential $T_2$ decay, 5 ms $T_2$ for measurement with TE=500 µs.
FIG. 3c is a graph showing bulk $T_2$ distribution of fully saturated sandstone #2, TE=500 µs, 256 echoes.
FIG. 3d is a graph showing an image of sandstone #2 employing the hybrid SE-SPI technique with TE=500 µs.

FIG. 2b illustrates a successful hybrid SE-SPI 1D image of fluid content in a porous media sample with a relatively long mean $T_2$. In cases where the mean $T_2$ is short, hybrid SE-SPI will suffer a serious image blurring. Sandstone #2 has a relatively short mean $T_2$ with the $T_2$ distribution reported in FIG. 3c. The experimental hybrid SE-SPI image, as shown in FIG. 3d, shows an unacceptable blur effect and image degradation is similar to that of FIG. 3a.

In samples where short $T_2$ relaxation time components are important, a centric scan SPRITE experiment or the $T_2$ mapping SE-SPI experiment outlined below are preferred.

B. $T_2$ Mapping SE-SPI

Figure 4:
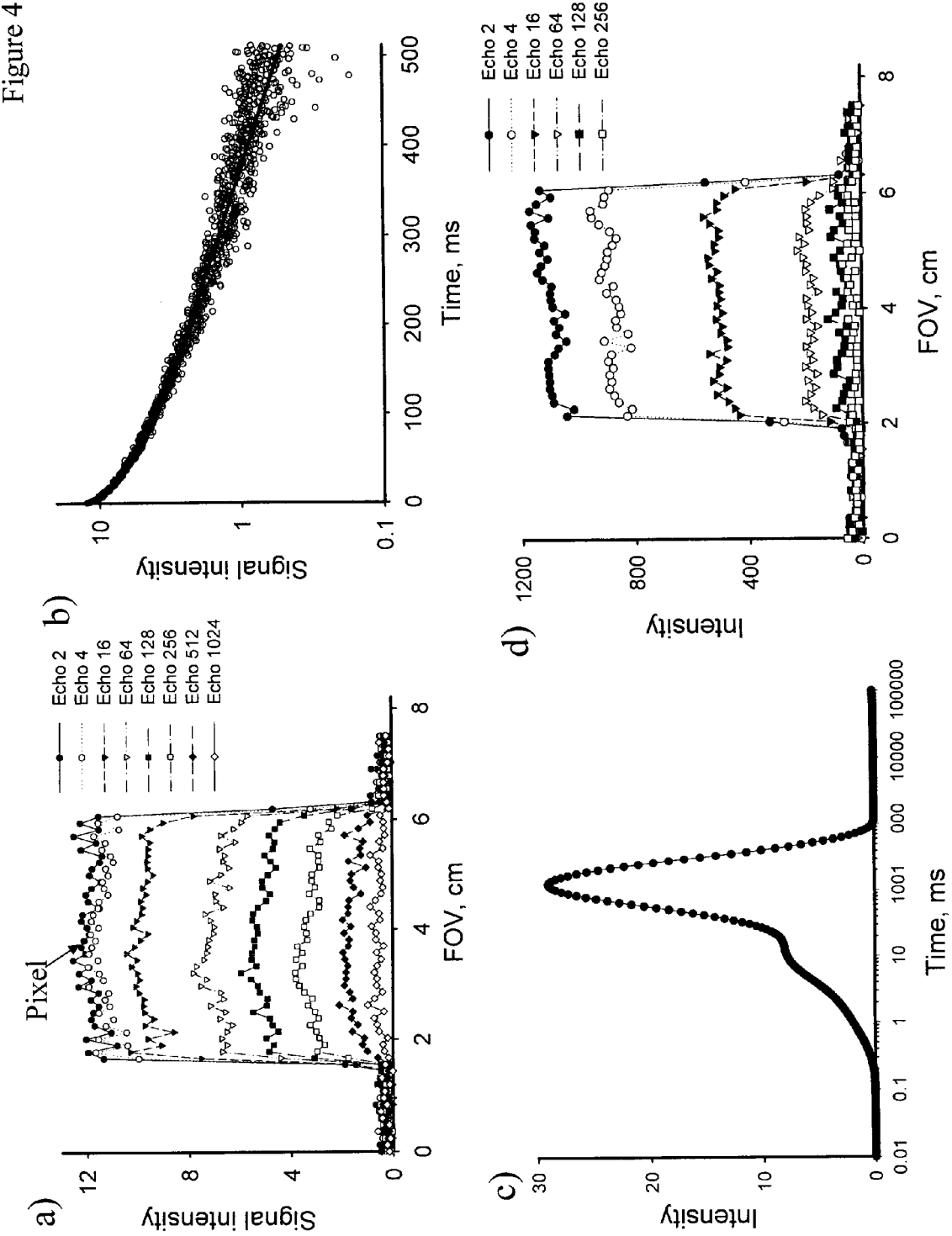
FIG. 4a is a graph showing $T_2$ weighted images of sandstone #1 acquired by the $T_2$ mapping pulse sequence of FIG. 1b in 10 mins with TE=500 µs.
FIG. 4b is a graph showing image intensity decay extracted from the marked pixel in FIG. 4a, for each $T_2$ weighted image.
FIG. 4c is a graph showing $T_2$ distribution resulting from an inverse Laplace transformation of the $T_2$ decay data in FIG. 4b.
FIG. 4d is a graph of $T_2$ weighted images of sandstone #2 acquired by the $T_2$ mapping pulse sequence of FIG. 1b, in 5 mins with TE=500 µs, 256 echoes.

By employing the pulse sequence of FIG. 1b, imaging of both sandstone reservoir core plugs was undertaken. The $T_2$ weighted 1D images of sandstone #1 are shown in FIG. 4a. 1024 echoes were generated for the $T_2$ 1D weighted images with a 10 minute acquisition time. The $T_2$ weighted 1D images do not suffer the $T_2$ related blurring of hybrid SE-SPI. The signal intensity decay extracted from a common pixel in each image is displayed in FIG. 4b. A total of 1024 images were collected from 1024 echoes. Inverse Laplace transformation of this $T_2$ decay yields the distribution reproduced as FIG. 4c. The bulk $T_2$ distribution in FIG. 2a and the local $T_2$ distribution are nearly identical proving the validity of the $T_2$ mapping method. Note that an echo time of 500 μs, as employed in this measurement, is similar to the echo times employed in many down-hole NMR logging tools. The $T_2$ weighted images of sandstone #2 with shorter $T_2$, are reproduced in FIG. 4d. Compared to FIG. 3d, a hybrid SE-SPI image, the 1D images of FIG. 4d from $T_2$ mapping SE-SPI do not suffer from a $T_2$ related blurring in spite of very short mean $T_2$. The spatially resolved $T_2$ distribution, (not shown), is very similar to the bulk $T_2$ distribution in FIG. 3c.

The pulse sequence of FIG. 1b is an alternate method of generating fluid content images, without edge blurring, but with a much longer image acquisition time than hybrid SE-SPI. A plot of the area under the $T_2$ distributions for each pixel is a map of fluid content. This provides a simple method of determining fluid content distribution for short $T_2$ samples when hybrid SE-SPI fails.

Application of Spatially Resolved $T_2$ Distribution Measurement

Figure 5:
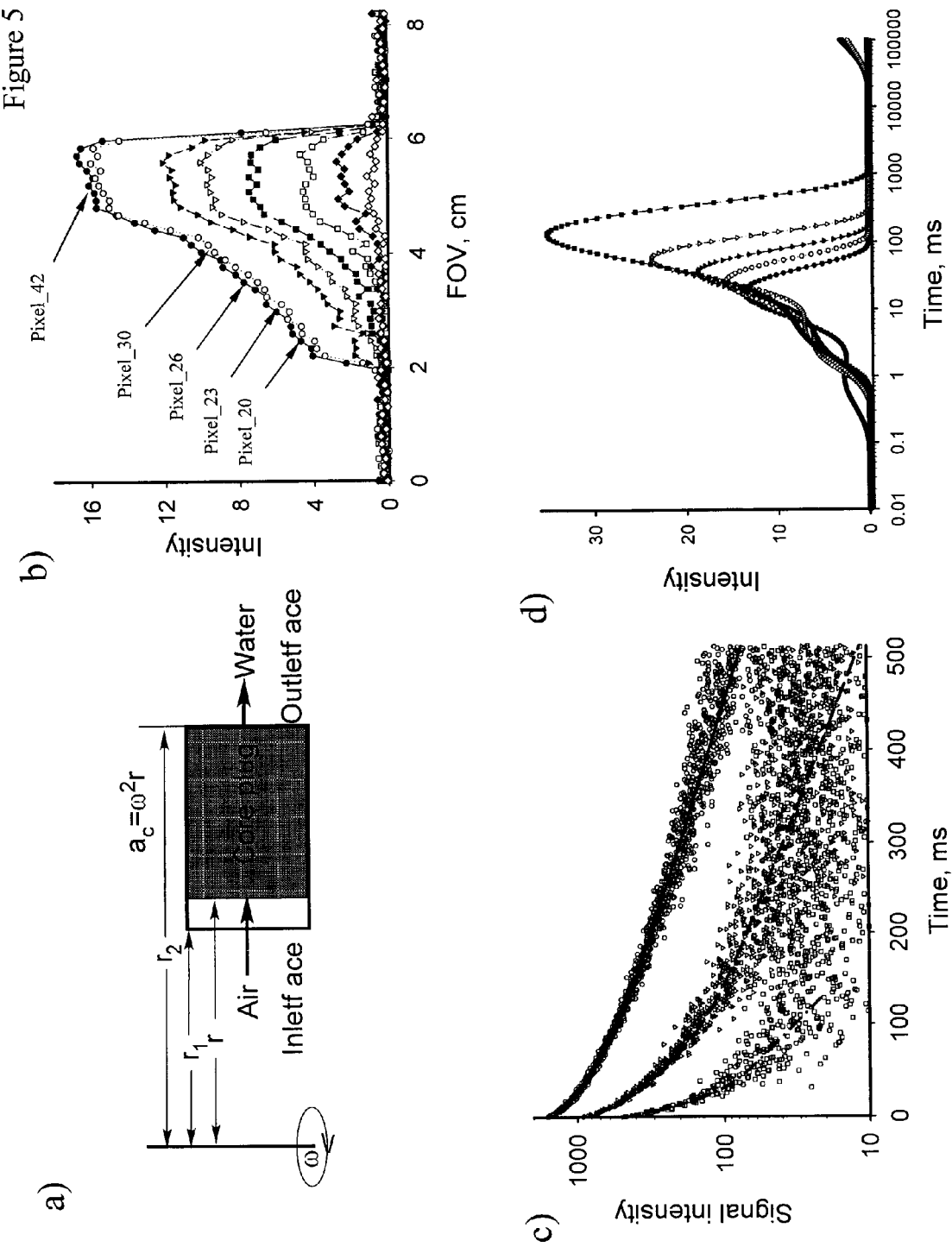
FIG. 5a is a schematic of a rock core plug centrifuge experiment.
FIG. 5b is a graph showing $T_2$ weighted images of sandstone #1 acquired after centrifugation with TE=500 µs, 1024 echoes where images are displayed for echo numbers •2, ○4, ▼16, △64, ■128, □256, ◆512 and ◇1024.
FIG. 5c is a graph showing signal decay from pixels □20, △30 and ○42 extracted from the experiment of FIG. 5b.
FIG. 5d is a graph showing $T_2$ distributions resulting from inverse Laplace transform of $T_2$ decay from pixels 20, 23, 26, 30 and 42.

The core plug sandstone sample #1, with $T_2$ distribution and $T_2$ weighted profiles shown in FIG. 2a and FIG. 2b respectively, was centrifuged at 500 rpm for 2 hrs. It was imaged with the method of FIG. 1b to generate $T_2$ weighted images. FIG. 5a illustrates the centrifugation process. During centrifugation in air, water drains from the left side to right side of the sample. Centrifugation is a common procedure in reservoir core analysis and introduces a spatially varying saturation [27]. The fluid content is higher on the right side of the profile because fluid accumulates at the outlet end of the sample due to capillary pressure effects and the outlet boundary condition. One anticipates from the centrifugation that larger pore sizes will be preferentially emptied due to capillary pressure effects, and that a change in the $T_2$ distribution should result from this desaturation.

The $T_2$ signal decay from pixels 20, 30 and 42, marked in FIG. 5b, is displayed in FIG. 5c. Since the experiment was implemented at low field with TE=500 μs, the diffusion contribution to transverse magnetization decay can be reasonably ignored. The $T_2$ distribution is thus dominated by the S/V of fluid occupied pores. FIG. 5c clearly reveals that the $T_2$ relaxation decay shifts to shorter lifetimes as water is removed by centrifugation. In FIG. 5d, an Inverse Laplace Transform was implemented to show the $T_2$ distribution from chosen pixels along the profiles of FIG. 5b. A shift of the $T_2$ distribution toward shorter lifetimes with reduced saturation is clearly observed in FIG. 5d. As anticipated, the area under the curve decreases with desaturation. The water does not significantly redistribute in this sample during the measurement duration of 10 mins.

Correlation Between the Local Logarithm Mean $T_2$ and the Local Saturation

The residual water saturation from each pixel of the core plug can be calculated from the ratio of the exponential fitting result of FIG. 5b and the corresponding pixel amplitude of FIG. 2b (fully saturated image). One could use FIG. 4a to determine the signal amplitude of the fully saturated image, however, the hybrid SE-SPI technique for pure density imaging acquisition is almost 30 times faster than the spatially resolved $T_2$ measurement.

Figure 6:
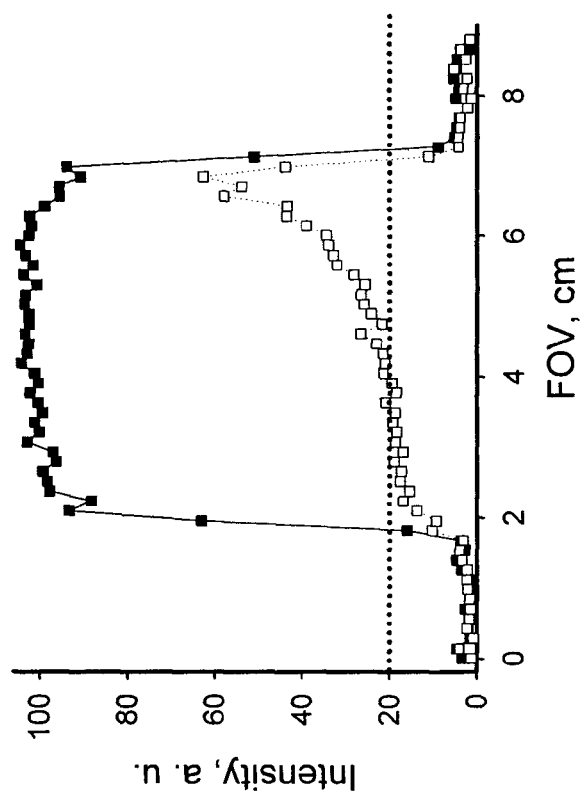
FIG. 6a is a graph showing local saturation determined from the ratio of the fully saturated hybrid SE-SPI image intensity to the local image intensity.
FIG. 6b is a graph showing hybrid SE-SPI images of fully saturated and desaturated sandstone #1 (48 hrs centrifugation at 1000 rpm).
Figure 6:
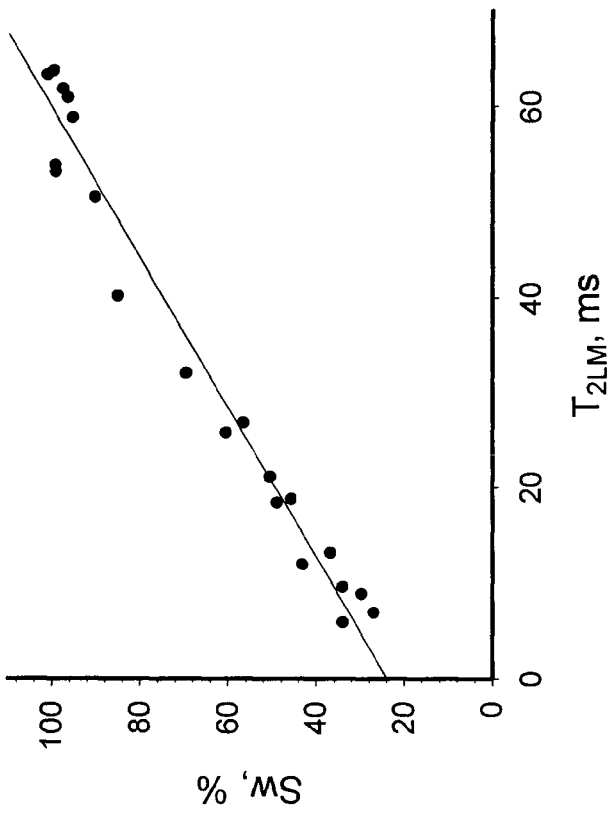

A linear relationship between the logarithm mean $T_2$ and the residual water saturation, pixel by pixel, was observed, and is reproduced in FIG. 6a. The logarithm mean $T_2$ is observed to shift linearly with local saturation. The intercept indicates the irreducible water saturation is 22.5%. The logarithm mean $T_2$, a common NMR core analysis and NMR logging parameter, is defined by Eq (5).

$$T_{2LM} = \exp\left[\frac{\sum_i [P_i \ln(T_{2i})]}{\sum_i P_i}\right] \quad (5)$$

The probabilities, $P_i$, are logarithmically spaced amplitudes in the $T_2$ distribution.

The explanation of this linear relationship is quite straightforward and may provide an important new core analysis measurement.

Empirical Model for Irreducible Water Saturation

The irreducible water volume from magnetic resonance logging tools provide the log analyst important information on a formation's permeability and its water-cut potential [14]. Coates et al. [14] has derived an equation for the irreducible water saturation (SWIRR) to aid NMR well logging data interpretation. The equation is reproduced as Eq (6).

$$\frac{1}{SWIRR} = mT_{2LM} + b \quad (6)$$

Where SWIRR is the irreducible water saturation (water that can not readily be removed from the sample) while $T_{2LM}$ is the logarithm mean $T_2$ (ms). The slope and intercept, m and b, are parameters to be determined by a calibration procedure before interpretation of the NMR well logging data.

Following Coates, Eq (7) can be derived:

$$\frac{S_{w(T_{2LM})}}{SWIRR} = mT_{2LM} + b \quad (7)$$

The difference between Coates's Eq (6) and Eq (7) comes from an alternate definition of the free fluid index (FFI which is free fluid volume). Coates defined FFI as being equal to $\phi(1-SWIRR)$ by assuming the reservoir rock is fully saturated with porosity $\phi$. FFI can be defined as being equal to $\phi(S_{w(T_{2LM})}-SWIRR)$ since the reservoir rock is partially saturated and contains less free fluid. The $S_{w(T_{2LM})}$ is the local residual water saturation and changes in this value will have associated changes in the logarithm mean $T_{2LM}$ in a rock centrifugation experiment.

According to Coates, in most cases the intercept b in Eq (6) can be constrained to 1. The same assumption modifies Eq (7) to Eq (8).

$$S_{w(T_{2LM})} = m \times SWIRR \times T_{2LM} + SWIRR \qquad (8)$$

Eq (8) suggests that a linear relationship between residual water saturation and the $T_{2LM}$ will exist with an intercept that is SWIRR. The m value is determined from the slope of the plot.

MRI Fast Calibration Result for Sandstone

Based on Eq (8), the intercept of FIG. 6a is 22.5 which indicates the SWIRR is 22.5%. The slope of 1.25 leads to an m value of 0.056 ms$^{-1}$. This experimental m agrees well with Coates's m value of 0.055 ms$^{-1}$ [14] when b was constrained to 1 for sandstones. In Coates's work [14], m was determined by bulk NMR measurement of nine different core plugs chosen from medium- to high-porosity sandstone formations. In the same work, Coates determined an m value of 0.0618 ms$^{-1}$ for a larger data set of 340 sandstones.

An alternative way to confirm Eq (8) is to independently determine the irreducible water saturation of the sandstone employed. Sandstone #1 was further centrifuged for 48 hours at 1000 rpm until an equilibrium state was reached. Hybrid SE-SPI was employed for fluid content imaging of the desaturated rock profile. Once again, fluid accumulates on the right hand side of the profile due to capillary pressure effects and the outlet boundary condition. The fully saturated and desaturated profiles in FIG. 6b indicate that the irreducible water saturation (SWIRR) is approximately 20% (dashed line), which agrees closely with the result of FIG. 6a. The SWIRR predicted from our MRI calibration procedure agrees reasonably well with the independent measurement of SWIRR.

MRI Calibration for Chalk (Limestone)

If b is not constrained, then Eq (7) could be used for the calibration. In this case, the irreducible water saturation SWIRR must be determined before the MRI centrifugation measurement. Once SWIRR is determined, simple linear regression, Eq (7), will determine the slope (m) and intercept (b) in Eq (7).

Figure 7:
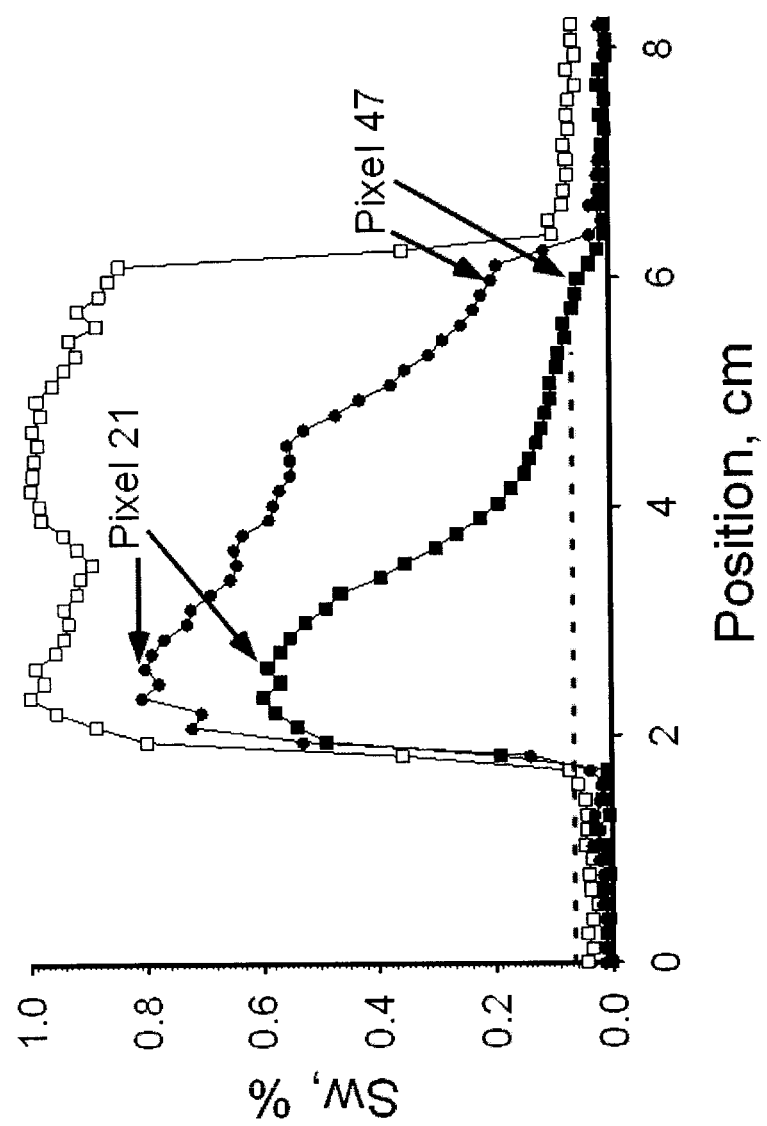
FIG. 7 is a graph showing SE-SPI images (first echo image) of □ fully saturated, • 2 hrs centrifuged at 500 rpm, and ■ 1 day centrifuged at 1500 rpm, chalk sample.
Figure 8:
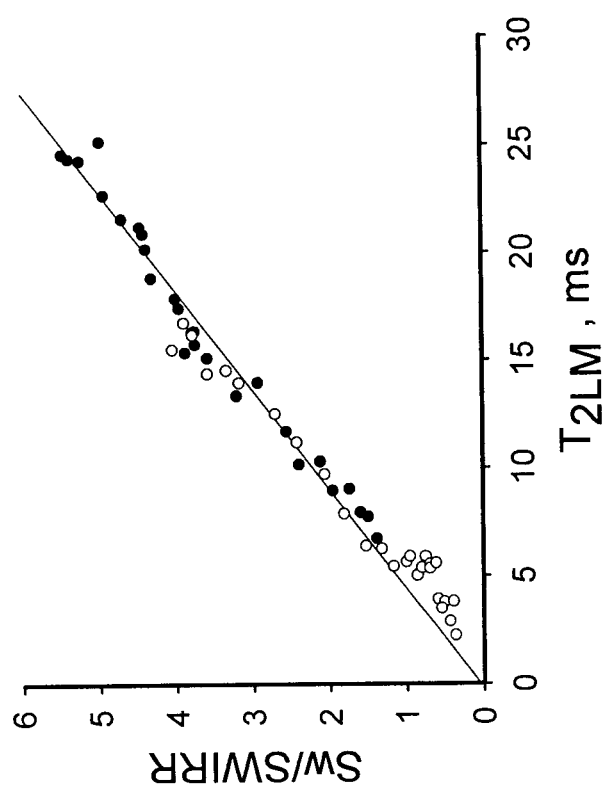
FIG. 8 is a graph showing local saturation of limestone determined from the ratio of the fully saturated SE-SPI image intensity to the local image intensity in the 2 hour and 1 day centrifuged chalk sample of FIG. 7.

The fully saturated, 2 hour-centrifuged and 1 day-centrifuged chalk MRI profiles shown in FIG. 7 indicate that the irreducible water saturation (SWIRR) of the chalk sample is approximately 8% (dotted line). FIG. 8 is a plot of pixel saturation and its corresponding logarithmic mean $T_2$ from pixel 21 to pixel 47 in FIG. 7. The filled points were extracted from the $T_2$ weighted images of 2 hour-centrifuged chalk sample profiles, (not shown), while the unfilled points were extracted from the $T_2$ weighted images of 1 day-centrifuged chalk sample profiles (not shown). The linear fitting in FIG. 8 was achieved by using data from 2 hour-centrifuged $T_2$ weighted profiles. The slope and intercept of FIG. 8 were 0.4 ms$^{-1}$ and 0.1 corresponding to m and b respectively in Eq (7).

FIG. 8 is convincing evidence that the linear relationship between the logarithmic mean $T_2$ and water saturation ($S_w$) is independent of the centrifuge speed and centrifuge time. The logarithmic mean $T_2$ is observed to shift linearly with local saturation. Therefore, the time duration for centrifugation equilibrium, the most time consuming part (several days) in the traditional Coates calibration method, is avoided in the new MRI method of this invention.

The Coates Eq (6) for irreducible saturation is a special case of Eq (7) proposed in this present invention. If $S_{w(T_{2LM})}$ in Eq (7) is equal to 100%, then Eq (7) will be identical to Eq (6) proposed by Coates. Both equations can be employed for rocks with a narrow $T_2$ distribution [14]. For rocks with a broad $T_2$ distribution, the linear relationship between $S_w$ and logarithm mean $T_2$ may not be true [28].

It will be understood by one skilled in the art that the methods of the present invention can be carried out using convention nuclear magnetic resonance equipment which can generate a magnetic field gradient which is linear with the integrated area. While the methods of the present invention have been described mainly with respect to the measurement of parameters in porous media, it will be understood by one skilled in the art that the methods of the present invention can also be used to measure one or more parameters in other media including but not limited to polymers, polymer formation processes, finishing and enamelling processes, coatings for pharmaceutical pills and freezing processes in foods by measuring density, $T_2$ distribution, or $T_2$ spatially resolved, individually or in some combination.

It will be further understood by one skilled in the art that the methods of the present invention can be adapted to higher dimensionality and can be used to permit magnetization preparation for variable contrast imaging.

The essential problem in quantitative fluid content MRI of porous media is the ill-controlled contrast which results from the $T_2$ distribution. According to one aspect, the present invention relates to a quantitative imaging method which avoids $T_2$ contrast, hybrid SE-SPI, and a second method, $T_2$ mapping SE-SPI, which permits determination of the $T_2$ distribution spatially resolved. A short evolution time FID yields the k-space origin data point, and the resulting image is essentially contrast free. Simulations show that quantitative images with minimal blurring are possible for petroleum reservoir core plug analysis when the dominant $T_2$ populations are longer than 5 ms. In samples where short $T_2$ relaxation time components are important, spin density imaging may be achieved with a centric scan SPRITE experiment or with the $T_2$ mapping SE-SPI method.

$T_2$ mapping SE-SPI technique permits fast determination of spatially resolved $T_2$ distributions in porous media with echo times of 1 ms or less. This method permits generation of several thousand $T_2$ weighted images in several minutes. Given the short echo time and low field strength, the transverse life time distribution measured will be a true reflection of the fluid occupied pore size distribution. Determination of local $T_2$ distribution yields a simultaneous local measurement of the fluid content.

A practical application of these two methods, imaging a centrifuged core plug, has demonstrated that these two methods provide reliable, robust and fast determination of the local saturation and spatially resolved $T_2$ distribution and together provide a promising new core analysis method.

The logarithm mean $T_2$, calculated from the $T_2$ distribution of individual pixels in the core plug, varies linearly with the water saturation. An empirical equation for the prediction of the irreducible water saturation in centrifuged core samples has been derived from permeability models.

The SE-SPI imaging methods according to the present invention provide quantitative analysis of local fluid saturation and the local $T_2$ distribution in porous media and are therefore very promising tools for petroleum reservoir core analysis and other areas of application.

Experimental Set-Up

All MRI measurements in the previous examples were performed on a MARAN DRX spectrometer (Oxford Instruments Ltd., Oxford, UK) console with a wide bore, horizontal bore superconducting magnet (GE NMR 2T/31 magnet system, charged to 0.35 T). The homemade 3 axis micro-imaging gradient set was 3" ID, with 0.67 Gauss/cm/A. A set of three Techron 8606 gradient amplifiers (GE medical system, Fremont, Calif., USA) were employed for the imaging measurement. A home-made 45 mm inner diameter bird cage RF probe was used with a 300W RE power amplifier (Resonance Instruments Ltd, Oxford, UK). All measurements were carried out at ambient magnet temperature 15° C.

The Acciss, Unifit and Impstar processing packages developed in the IDL programming environment by the University of New Brunswick MRI Centre were employed for image reconstruction, fitting and display. 2D Laplace Inversion Software (Magritek Ltd New Zealand) was employed for determining the relaxation time distributions.

A Hermle bench top centrifuge, (Z513K, Wehingen, Germany) was employed for the centrifugation experiment. The centrifugation, for the $T_2$ distribution measurement, sample, was 2 hrs at 500 rpm. The SWIRR centrifugation experiment was undertaken in the same centrifuge for 48 bra at 1000 rpm.

Reservoir core plug sandstone #1 had a porosity of 20%, 5.5 cm length, 2.5 cm diameter. After water saturation, the relaxation times were $T_2^*$=778 μs, $T_{2(1)}$=39.4 ms, 53%; $T_{2(2)}$=228 ms, 47%, with $T_2$ fit to a bi-exponential relaxation model. The $T_1$ was essentially single exponential at 100 ms.

The second reservoir core plug, sandstone sample #2, had a porosity of 20%, 5.5 cm length, 2.5 cm diameter. After water saturation, the relaxation times were $T_2^*$=270 μs, $T_{2(1)}$=4.2 ms, 62%; $T_{2(2)}$=42 ms, 38%, with $T_2$ fit to a bi-exponential relaxation model. The $T_1$ was essentially single exponential at 100 ms.

Hybrid SE-SPI imaging parameters were: 90° pulse length 17.5 μs; filter width 125000 Hz; filter dead time 26 μs; FOV was 10 cm; maximum gradient strength was 5 G/cm. 64 k-space points were acquired with a phase encoding time of 150 μs; Single point acquisition was employed on the echo for image acquisition. Four signal averages were acquired in an imaging time of 20 s.

SE-SPI $T_2$ imaging parameters were: 90° pulse length 17.5 μs; phase encoding time was 150 μs; filter width was 125000 Hz; filter dead time was 26 μs; The filter width was maintained at the values of the hybrid SE-SPI acquisition for experimental consistency. The FOV was 10 cm with a maximum gradient, strength of 5 G/cm. Single point acquisition was employed on the echo with four signal averages. 1024 echoes (images) were acquired for sandstone #1, 256 for sandstone #2. The echo time was 500 μs, with an imaging time of 10 mins for sandstone #1 and 5 min for sandstone #2.

The SE-SPI phase cycle, for both imaging techniques, was a simple bulk CPMG phase cycle. The 90° pulse was x, y, −x, −y with the 180° pulse set to y, y, −y, −y for a receiver phase of x, y, −x, −y.

Figure 9:
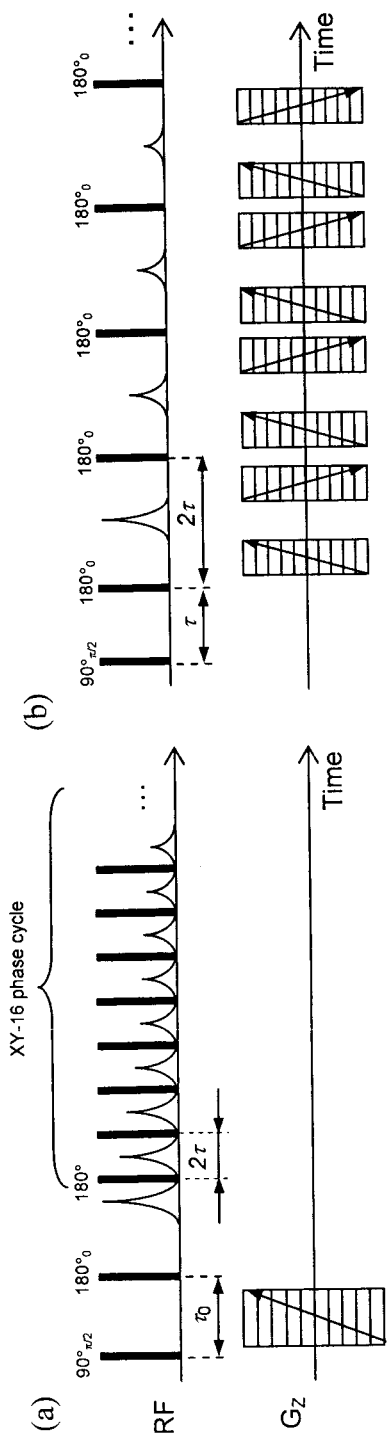
FIG. 9(a) is a diagram of sequence #1.
FIG. 9(b) is a diagram of sequence #2.
Figure 10:
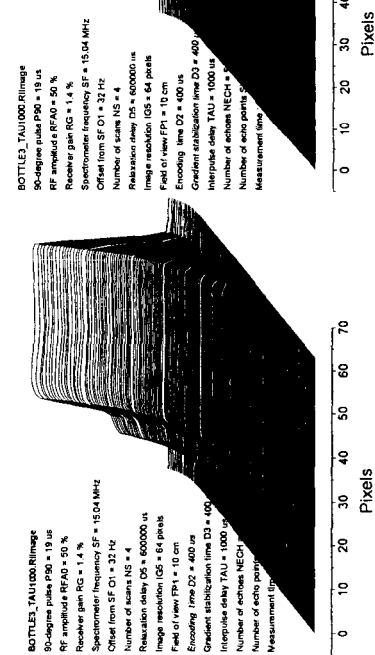
FIG. 10(a) is a profile of a 30 ml vial of $GdCl_3$-doped water by sequence #1.
FIG. 10(b) is a profile of a 30 ml vial of $GdCl_3$-doped water by sequence #2.
FIG. 10(c) is a graph of $T_2$-signals from middle pixels in FIG. 10(a) and FIG. 10(b).
FIG. 10(d) is a graph of $T_2$ distributions computed from the $T_2$-signals of FIG. 10(c).
Figure 10:
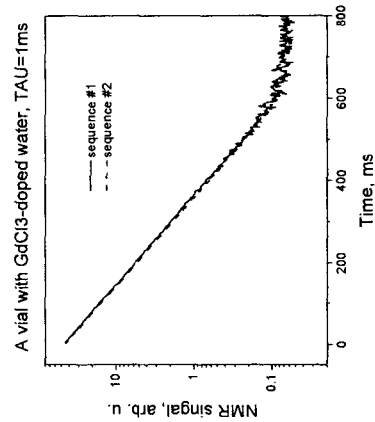
Figure 10:
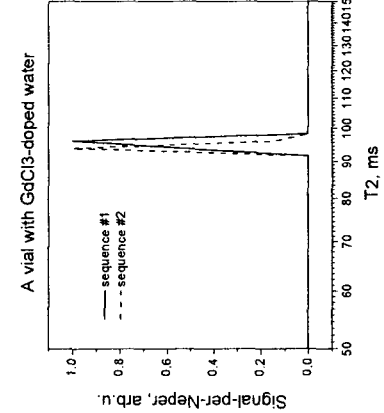

Comparison of Two Pulse Sequences for 1-D $T_2$ Mapping with a Purely Phase Encoding In order to infer whether sequence #1 of FIG. 9 and sequence #2 of FIG. 10 give alike $T_2$ distributions and profiles' quality, sequence #2 was replaced by sequence #1 on DRX systems provided the interpulse delay $2\tau$ is the same.

Sequence #1 is used because having a pair of gradients between refocusing pulses in sequence #2 imposes a restriction on the lower limit of $2\tau$. For instance, the hardware used in the embodiments of this invention requires at least 300-400 μs for the gradient to be established and another 300-400 μs for the delay between turning off the gradient and starting an echo acquisition (for eddy currents to settle). Setting those delays shorter may result in distorted profiles. This, together with a multi-point acquisition and finite RF-pulses, limits $2\tau$ by approximately 2 ms. Having large interpulse delays means a seldom sampling of $T_2$-signal, which may be problematic for an accurate measurement of $T_2$ distribution by Inverse Laplace Transform (ILT). Besides, the greater the $2\tau$, the greater a diffusion attenuation term in $T_2$ (roughly proportional to $\tau^2$). Sequence #1 has such a restriction only for the very first interpulse delay, while the following delays can be made as short as required for the acquisition of the given number of echo points. A further reason to use sequence #1 is because effective areas of the paired gradients need to be matched to properly cancel the phase shift after an echo acquisition in sequence #2. This problem is avoided in sequence #1.

Overall, it was found that sequence #1 does the same work as sequence #2, and may even provide a better profile quality. Hence, sequence #1 can be used instead of sequence #2 for 1-D $T_2$ mapping without loss on exchange.

Experiments

Measurements were conducted on the MaranGE DRX system (v=15 MHz), using the main GE-gradient set. An r.f. probe used was a 54-mm wide probe, a 90° pulse duration being 19 μs. It should be noted that the hardware and experimental parameters used in this invention are not the same as that used in prior art [29], where sequence #2 was first used. Composite pulses were employed to compensate r.f. field errors, namely, the sequences $45_{\pi/2}90_090_{3\pi/2}45_0$ for a composite 90° pulse and $180_0180_{2\pi/3}180_0$ for a composite 180° pulse [30]. Using these composite pulses was found to improve the image quality in both sequences #1 and #2. However, they did not compensate for off-resonance errors and therefore did not exclude using respective phase cycles (see below). Number of echoes varied from 128 to 768, depending on the sample. The 180° interpulse delay $2\tau$ was set to 2 ms, due to the requirements mentioned above. The phase encode dimension was 64.

An XY-16 phase cycling scheme $(\pi/2, \pi, \pi/2, \pi, \pi, \pi/2, \pi, \pi/2, 3\pi/2, 0\ 3\pi/2, 0, 0, 3\pi/2, 0, 3\pi/2)^n$ [19] was applied for 180° pulses in sequence #1, and a regular CPMG phase scheme with fixed phases in sequence #2 (as shown in FIG. 9). These phases added to those defined in the composite pulses will give a resultant phase table. Using the XY-16 phase cycle in sequence #1 is crucial for the 'encode once' implementation. XY-16 is capable to preserve all three components of magnetization under refocusing [31, 15], thus the phase shift that is introduced by the encode gradient after the first 90° pulse remains the same in subsequent echoes. This is not so for a regular CPMG phase scheme, where the magnetization may oscillate around $B_1$ due to an accumulative off-resonance error, which deteriorates the initial phase shift. This is why one has to cancel the phase shift after every echo acquisition in sequence #2, by applying the second gradient of the same amplitude but in the opposite direction (FIG. 9b).

To increase signal-to-noise ratio, 20 points were acquired from every echo signal, symmetrically with respect to the echo's centre. That is, every echo gives 20 separate k-space signals. The signals are then reconstructed with Fast Fourier Transform (FFT) into 20 individual profiles, which are finally added up into a single profile corresponding to the given echo number. This averaging scheme was found to increase the image intensity almost proportionally to the number of echo points. One will note that such a multiple-point acquisition is the basis for a $T_2^*$ mapping, since it introduces a $T_2^*$ decay bias in the k-space signal. Prior to FFT, k-space signals were multiplied by a Hanning window function to remove ringing artifacts in the profiles due to a k-space signal truncation.

Test #1: A Vial with $GdCl_3$-Doped Water

In one embodiment of this invention, the sequences were compared for their ability to measure a single-exponential relaxation. FIG. 10 shows profiles of a 30 ml vial of $GdCl_3$-doped water by sequence #1 (FIG. 10a) and sequence #2

(FIG. 10b). 512 rofiles were acquired in 7 min (NS=4). Overall, the profile quality by sequence #1 seems better than by sequence #2. In particular, the profiles by sequence #1 are quite regular, while those by sequence #2 are not (mostly close to the edges). The latter is likely to be a consequence of a poor gradients' match (see above). FIG. 10c shows $T_2$-signals from the middle pixels of the profiles by different sequences. The signals exhibit the same slope, corresponding to $T_2$=94 ms (FIG. 10d), and the same noise level.

Test #2: Berea Sandstone Saturated With Water

Figure 11:
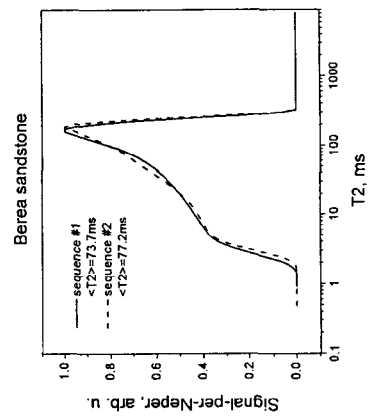
FIG. 11(a) is a profile of the Berea sandstone by sequence #1.
FIG. 11(b) is a profile of the Berea sandstone by sequence #2.
FIG. 11(c) is a graph of $T_2$ distributions computed from middle point's decays.
Figure 11:
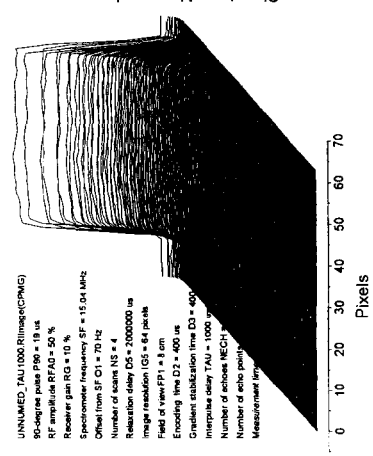
Figure 11:
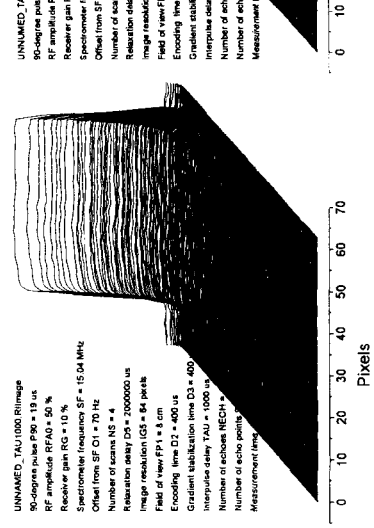

In another embodiment of this invention, the sequences were tested for measuring $T_2$-distributions. The first sample was Berea sandstone, made into 5.2×2.5 cm cylinder, saturated with distilled water. FIGS. 11a and 11b show profiles of the sandstone by sequences #1 and #2, respectively. Again, the profiles by sequence #1 look more regular than those by sequence #2. FIG. 11c shows $T_2$ distributions computed from the middle point of the profiles in FIG. 11a and FIG. 11b. The distributions appear identical and give close mean $T_2$ values (shown on the panel of FIG. 11c).

Test #3: An Eraser

Figure 12:
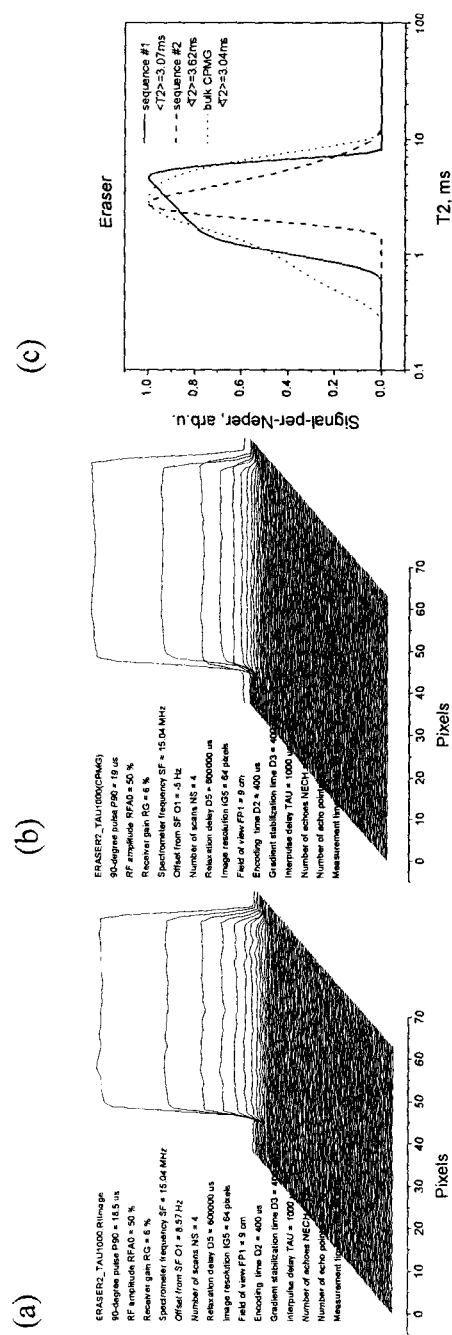
FIG. 12(a) is a profile of the eraser by sequence #1.
FIG. 12(b) is a profile of the eraser by sequence #2.
FIG. 12(c) is a graph of $T_2$ distributions computed from the middle point's decay, in comparison to a bulk CFMG measurement.

In yet another embodiment of this invention, an eraser, characterized as a 6.2 cm long brick of rubber, was used as a sample. FIGS. 12a and 12b show profiles of the eraser by sequences #1 and #2, respectively. 128 profiles were acquired in less than 4 min. The profiles in FIGS. 12a and FIG. 12b look similar, except that the profiles in FIG. 12b vary in width a little from one profile to the other. $T_2$ distributions computed from the middle pixel's decays are shown in FIG. 12c, in comparison to a bulk CPMG measurement. Neither of the two sequences reproduces the bulk CPMG data, though sequence #1 provides the same mean $T_2$ value as the bulk CPMG.

REFERENCES

[1] S. Chen, K. Kim, F. Qin, and A. T. Watson, Quantitative NMR Imaging of Multiphase Flow in Porous Media, Magn. Reson. Imag. 10 (1992) 815-826.

[2] F. Marica, Q. Chen, A. Hamilton, C. Hall, T. Al, and B. J. Balcom, Spatially Resolved Measurement of Rock Core Porosity, J. Magn. Reson. 178 (2006) 136-141.

[3] B. J. Balcom, R. P. MacGregor, S. D. Beyea, D. P. Green, R. L. Armstrong, T. W. Bremner, Single-Point Ramped Imaging with $T_1$ Enhancement (SPRITE), J. Magn. Reson. A 123 (1996) 131-135.

[4] Z. Zhang, A. E. Marble, B. MacMillan, K. Promislow, J. Martin, H. Wang, and B. J. Balcom, Spatial and temporal mapping of water content across Nafion membranes under wetting and drying conditions, J. Magn. Reson. (2008) (in press).

[5] S. Gravina, D. G. Cory, Sensitivity and Resolution of Constant-Time Imaging, J. Magn. Reson., B 104, (1994) 53-61.

[6] Y. Cheng, M. B. MacMillan, R. P. MacGregor, and B. J. Balcom, Direct Detection of Hydrocarbon Displacement in a Model Porous Soil with Magnetic Resonance Imaging, Analytical Chemistry 77 (2005) 1824-1830.

[7] Y. Cheng, $^{13}$C Magnetic Resonance Imaging of Physico-Chemical Processes, UNB Ph.D thesis (2005) 93-114

[8] A. V. Ouriadov, R. P. MacGregor, and B. J. Balcom, Thin Film MRI-High Resolution Depth Imaging with a Local Surface Coil and Spin Echo SPI, J. Magn. Reson., 169 (2004) 174-186.

[9] S. D. Beyea, B. J. Balcom, I. V. Mastikhin, T. W. Bremner, R. L. Armstrong, and P. E. Grattan-Bellew, Imaging of Heterogeneous Materials with a Turbo Spin Echo Single-Point Imaging Technique, J. Magn. Reson. 144 (2000) 255-265.

[10] R. L. Kleinberg, W. E. Kenyon, P. P. Mitra, Mechanism of NMR Relaxation of Fluids in Rock, J. Magn. Reson., 108 (1994) 206-214.

[11] Y. Song, S. Ryu and P. N. Sen, Determining multiple length scales in rocks, Nature, 406 (2000) 178-181.

[12] R. L. Kleinberg, Utility of NMR $T_2$ Distribution, Connection with Capillary Pressure, Clay Effect, and Determination of the Surface Relaxivity Parameter $\rho_2$, Magn. Reson. Imag. 14 (1996) 761-767.

[13] D. Chang, H. Vinegar, C. Morriss, C. Straley, Effective Porosity, Producible Fluid and Permeability in Carbonates from NMR Logging, The Log Analyst, 38 (1997) 60-72,

[14] G. R. Coates, D. Marschall, and D. Mardon, J. Galford, A New Characterization of Bulk-Volume Irreducible Water Using Magnetic Resonance, The Log Analyst, 39 (1998) 51-63.

[15] C. S. Poon, R. M. Henkelman, Practical $T_2$ Quantization for Clinical Applications. J. Magn. Reason. Imaging, 2 (1992) 541-553.

[16] A. P. Crawley, M. L. Wood, R. M. Henkelman, Elimination of Transverse Coherences in FLASH MRI, Magn. Resort. Med. 8 (1988) 248-260.

[17] A. A. Maudsley, Modified Carr-Purcell-Meiboom-Gill Sequence for NMR Imaging Fourier Imaging Applications, J. Magn. Reson. 69 (1986) 488-491.

[18] X. Wan, D. L Parker, J. N. Lee, H. R. Buswell and G. T. Gullberg, Reduction of Phase Error Ghosting Artifacts in Thin Slice Fast Spin Echo Imaging, Magn. Reson. Med. 34 (1995) 632-638.

[19] T. Gullion, The effect of amplitude imbalance on compensated Carr-Purcell sequence, J. Magn. Reson. 101 (1993) 320-323.

[20] H. T. Edzes, D. Dusschoten, H. V. As., Quantitative $T_2$ Imaging of Plant Tissues By Means Of Multi-Echo MRI Microscopy, Magn. Resort. Imag. 16 2 (1998) 185-196.

[21] L. L. Latour, R. L. Kleinberg, P. P. Mitra, C. H. Sotak, Pore-Size Distributions and Tortuosity in Heterogeneous Porous Media, J. Magn. Reson. 112 (1995) 83-91.

[22] R. L. Kleinberg, M. A. Horsfield, Transverse Relaxation Processes in Porous Sedimentary Rock, J. Magn. Reson. 881 (1990) 949.

[23] P. Wong, Methods in the Physics of Porous Media, Academic Press, New York, (1999) 337-385.

[24] D. J. Goodyear, M. Shea, S. D. Beyea, N. J. Shah, and B. J. Balcom, Single Point Measurements of Magnetic Field Gradient Waveform", J. Magn. Reson. 163 (2003) 1-7.

[25] K. Deka, M. B. MacMillan, A. V. Ouriadov, I. V. Mastikhin, J. J. Young, P, M. Glover, G. R. Ziegler, and B. J. Balcom, Quantitative Density Profiling with Pure Phase Encoding and a Dedicated 1D Gradient, J. Magn. Reson. 178 (2006) 25-32.

[26] M. C. Jeruchim, P. Balaban, K. Sam Shanmugan, Simulation of Communication Systems, Plenum Press, New York, N.Y., USA, 1992.

[27] Q. Chen, and B. J. Balcom, Measurement of Rock Core Capillary Pressure Curves Using a Single-Speed Centrifuge and One Dimensional Magnetic Resonance Imaging, J. Chem. Phys. 122 (2005) 214720-214728.

[28] L. W, Lake and E. D. Holstein, Petroleum Engineering Handbook, Society of Petroleum Engineers, TX, USA, (2007) V 289-V 356.

[29] Li, L., H. Han, and B. J. Balcom, Spin echo SPI methods for quantitative analysis of fluids in porous media. Journal Of Magnetic Resonance, 2009.198: p. 252-260.

[30] Levitt, M. H., COMPOSITE PULSES. Progress in Nuclear Magnetic Resonance Spectroscopy, 1986.18: p. 61-122.

[31] Windt, C. W., F. J. Vergeldt, and H. Van As, Correlated displacement-T-2 MRI by means of a Pulsed Field Gradient-Multi Spin Echo method. Journal Of Magnetic Resonance, 2007. 185(2): p. 230-239.

TABLE 1

Comparison of Hybrid SE-SPI and SPRITE fluid content images for sandstone sample # 1

| Image type | Pulse flip angle | Filter width Hz | Acquisition point | Number of scans | S/N | Acquisition time, s | $\eta$* |
|---|---|---|---|---|---|---|---|
| Hybrid SE-SPI | 90° | 125000 | 1 | 4 | 32 | 12 | 7.15 |
| DHK SPRITE | 20° | 200000 | 1 | 64 | 30 | 137 | 2.56 |

*$\eta$ is the sensitivity defined as $\eta = \dfrac{S/N}{\sqrt{t}}$

We claim:

1. A method of determining a spatially resolved $T_2$ distribution of a sample by imaging at least a portion of the sample using a spin-echo single-point imaging (SE-SPI) pulse sequence comprising the steps of:
    (a) applying a pure phase encoding to the SE-SPI pulse sequence;
    (b) acquiring a multiplicity of spin-echoes;
    (c) generating a $T_2$ weighted image of each of the spin-echoes using Fourier transform; and
    (d) determining a spatially resolved $T_2$ distribution for the sample from the images using inverse Laplace transformation.

2. The method according to claim 1, wherein step (a) of applying the pure phase encoding comprises applying the phase encoding and a phase unwinding gradient to each spin-echo.

3. The method according to claim 2, wherein applying the phase encoding and the phase unwinding gradient to each spin-echo comprising using a Carr-Purcell-Meiboom-Gill (CPMG) multi-echo sequence.

4. The method according to claim 3, wherein the phase encoding gradient and phase unwinding gradient are applied between refocusing pulses in the CPMG sequence.

5. The method according to claim 4, wherein fixed RF pulse phases are used in the CPMG sequence.

6. The method according to claim 2 further comprising varying the pure phase encoding and repeating steps (a) to (c).

7. The method according to claim 1, wherein step (a) of applying the pure phase encoding comprises applying the phase encoding gradient to the SE-SPI pulse sequence using an XY-16 sequence and composite RF pulses.

8. The method according to claim 7, further comprising repeating steps (a) to (c) with a pure phase encoding having a different amplitude.

9. The method according to claim 1, wherein the phase encoding gradient is applied once during the SE-SPI pulse sequence.

10. The method according to claim 9, wherein the phase encoding gradient is applied after the first inter-pulse delay of the SE-SPI pulse sequence.

11. The method according to claim 1, wherein the echo time in the SE-SPI pulse sequence is less than 1 ms.

12. The method according to claim 1, wherein the sample is at least partially saturated with a fluid, and further comprising the step of:
    using an external force to build up a distribution of saturations in one dimension in the sample.

13. The method according to claim 12, comprising using the spatially resolved $T_2$ distribution to determine the $T_2$ distribution as a function of capillary pressure.

14. The method according to claim 12, further comprising the step of generating an image of a local saturation of the sample by integration of the $T_2$ distribution curve or by fitting the spatially resolved decay curve to three exponentials and extrapolating to zero.

15. The method according to claim 12, further comprising the step of correlating the local log mean $T_2$ distribution with local saturation to determine the irreducible water saturation of the sample.

16. The method according to claim 1, further comprising:
    deriving the parameter from the spatially resolved $T_2$ distribution.

17. The method according to claim 16, wherein the sample is at least partially saturated with a fluid, and further comprising the step of using an external force to build up a distribution of saturations in one dimension in the sample.

18. The method according to claim 17, wherein the step of deriving the parameter in step (e) comprising using the spatially resolved $T_2$ distribution to determine the $T_2$ distribution as a function of capillary pressure.

* * * * *